(12) United States Patent
Yuan et al.

(10) Patent No.: US 12,333,424 B2
(45) Date of Patent: Jun. 17, 2025

(54) DETERMINING CEREAL GRAIN CROP YIELD BASED ON CEREAL GRAIN TRAIT VALUE(S)

(71) Applicant: Deere & Company, Moline, IL (US)

(72) Inventors: Zhiqiang Yuan, San Jose, CA (US); Theodore Monyak, San Francisco, CA (US)

(73) Assignee: Deere & Company, Moline, IL (US)

( * ) Notice: Subject to any disclaimer, the term of this patent is extended or adjusted under 35 U.S.C. 154(b) by 729 days.

(21) Appl. No.: 17/072,941

(22) Filed: Oct. 16, 2020

(65) Prior Publication Data

US 2022/0121919 A1      Apr. 21, 2022

(51) Int. Cl.
| | |
|---|---|
| G06N 3/08 | (2023.01) |
| G01N 33/00 | (2006.01) |
| G01N 33/10 | (2006.01) |
| G06V 20/10 | (2022.01) |

(52) U.S. Cl.
CPC ........... *G06N 3/08* (2013.01); *G01N 33/0098* (2013.01); *G01N 33/10* (2013.01); *G06V 20/188* (2022.01)

(58) Field of Classification Search
CPC .... G06N 3/08; G06V 20/188; G01N 33/0098; G01N 33/10
USPC ........................................................ 705/7.11
See application file for complete search history.

(56) References Cited

U.S. PATENT DOCUMENTS

| | | | |
|---|---|---|---|
| 5,897,619 A | 4/1999 | Hargrove et al. | |
| 9,984,455 B1* | 5/2018 | Fox ........................ | B64C 31/024 |
| 2005/0192760 A1 | 9/2005 | Dunlap | |
| 2017/0251589 A1 | 9/2017 | Tippery et al. | |
| 2018/0025480 A1 | 1/2018 | Dingle et al. | |
| 2018/0137357 A1* | 5/2018 | Margalit ............... | G06V 20/188 |
| 2018/0189564 A1* | 7/2018 | Freitag .................. | G06F 18/214 |

(Continued)

FOREIGN PATENT DOCUMENTS

| | | | |
|---|---|---|---|
| JP | 2003006612 | | 1/2003 |
| JP | 2020150887 A | * | 9/2020 |

OTHER PUBLICATIONS

GRDC (Grains Research & Development Corporation); Cereal Growth Stages; ISBN 1-875477-40-3; 40 pages; dated Sep. 2005.

(Continued)

*Primary Examiner* — Abdallah A El-Hage Hassan
(74) *Attorney, Agent, or Firm* — HANLEY, FLIGHT & ZIMMERMAN, LLC

(57) ABSTRACT

Techniques are disclosed that enable generating a predicted yield for a cereal grain crop based on one or more traits extracted from image(s) of the cereal grain crop. Various implementations include determining a heading trait value based on the number of identified spikelets, where the spikelets are identified by processing the image(s) of the cereal grain crop using a spikelet detection model. Additional or alternative implementations include generating a predicted cereal grain crop yield based on one or more additional or alternative trait values such as one or more heading values, one or more projected leaf area values, one or more stand spacing values, one or more wheat rust values, one or more maturity detection values, one or more intercropping phenotyping values extracted cereal grains intercropped with other crops, one or more additional or alternative trait output values, and/or combinations thereof.

14 Claims, 7 Drawing Sheets

(56) References Cited

U.S. PATENT DOCUMENTS

| | | |
|---|---|---|
| 2018/0211156 A1 | 7/2018 | Guan et al. |
| 2018/0293671 A1 | 10/2018 | Murr et al. |
| 2018/0308229 A1 | 10/2018 | Winkler et al. |
| 2023/0169640 A1* | 6/2023 | Wake .................. A01G 7/00 382/110 |

OTHER PUBLICATIONS

Dr. Patil, J. et al.; Paideuma Journal; AISSMS Institutte of Information Technology, Pune; India Department of Information Technology, Crop Prediction and Disease Detection Using Machine Learning; vol. XIII, Issue VII; pp. 139-144; dated 2020.

Reeves, D.L., et al.; How an Oat Plant Develops; Open PRAIRIE: Open Public Research Access Institutional Repository and Information Exchange; South Dakota State University Apricultural Experiment Station; 17 pages; dated Oct. 1, 1976.

Rajala, A. et al.; Pollination dynamics, grain weight and grain cell number within the inflorescence and spikelet in oat and wheat; Agricultural Sciences; vol. 2, No. 3, 283-290; dated 2011.

Qiu, R. et al.; Detection of Fusarium Head Blight in Wheat Using a Deep Neural Network and Color Imaging; Remote Sensing; 20 pages; dated 2019.

Lee, W.S.; Citrus Yield Mapping System in Natural Outdoor Scenes using the Watershed Transform; dated Jul. 2006.

Calafell, Davinia; Application of image processing methodologies for fruit detection and analysis; Universitat de Lleida; 86 pages; dated Jul. 2014.

Climate Fieldview—Yield Analysis; Video retrieved from https://www.youtube.com/watch?v=G6M-YGolxeA; dated Nov. 1, 2017.

Google Glass—New Tool for Ag; Video retrieved from https://www.youtube.com/watch?v=drypBC4bzLg; dated Oct. 31, 2014.

Grassi, Mathew; Google Glass: New Tool for Ag; retrieved from https://www.croplife.com/precision/google-glass-new-tool-or-toy-for-ag/; dated Oct. 8, 2014.

Klompenburg, Thomas et al.; Crop yield prediction using machine learning: A systematic literature review; Computers and Electronics in Agriculture; 18 pages; dated 2020.

Alkhudaydi, T. et al.; "SpikeletFCN: Counting Spikelets from Infield Wheat Crop Images Using Fully Convolutional Networks;" Advances in Databases and Information Systems; [Lecture Notes in Computer Science; Lect. Notes Computer]; Springer International Publishing; 11 pages; dated May 24, 2019.

European Patent Office; International Search Report and Written Opinion of PCT Application No. PCT/US2021/054590; 10 pages; dated Jan. 28, 2022.

* cited by examiner

DETERMINING CEREAL GRAIN CROP YIELD BASED ON CEREAL GRAIN TRAIT VALUE(S)

BACKGROUND

As agricultural data mining and planning becomes more commonplace, the amount of data analyzed, and the number of sources providing that data, is increasing rapidly. Trait extraction generally refers to processing a set of images (e.g., a set of images capturing a field while a crop is growing) to identify and/or detect phenotypic attributes which may be of interest to a crop breeder. Identification and/or detection of phenotypic attributes may be useful to breeders who, for example, may be conducting trials of competing varieties of a crop by providing measurements by which to compare the varieties. Existing trait extraction techniques may be arduous and time-consuming, prone to human error and subjectivity.

SUMMARY

Implementations disclosed herein are directed towards automatically extracting one or more traits from images of cereal grains. In some implementations, the extracted trait(s) can be used to generate a predicted yield of a cereal grain crop. For example, the one or more automatically extracted traits can include a heading value, a projected leaf area, a stand spacing value, a rust score, a maturity detection value, a phenotyping value extracted from plots of cereal grains intercropped with other crops, one or more additional or alternative traits, and/or combinations thereof.

Cereals are grasses which may be cultivated for the edible components of their grain (i.e., the endosperm, germ, bran, etc.). Cereal grains include wheat, maize, rice, barley, oats, rye, sorghum, etc. In some implementations, one or more images may capture at least a portion of a cereal grain crop. For example, a cereal grain field can be divided into four quadrants and each quadrant can be captured in a corresponding image. Additionally or alternatively, in some implementations, a sequence of images can be captured of the cereal grain plot over time. For example, an image of the cereal grain plot can be captured each day during the growing season. For instance, a first image of the cereal grain plot can be captured the day the cereal grain crop is planted, an additional image of the cereal grain plot can be captured each day of the growing season, and a final image of the cereal grain plot can be captured the day the cereal grain is harvested.

In some implementations, heading can refer to the degree of spikelet growth on a cereal plant (e.g., the degree of spikelet growth on an oat plant). The start of heading can indicate the date that spikelets begin to grow on the cereal branches. Additionally or alternatively, full heading can indicate the date on which new spikelets stop appearing. In some implementations, a heading value can indicate the relative degree of heading growth on a plant. For example, a plot can be referred to as 50% headed when half of the total spikelets for the season have grown in on the plants in the plot.

In some implementations, a heading value can be automatically extracted from one or more images using a spikelet detection model. The spikelet detection model can be trained to identify the location of one or more spikelets in an image (e.g., draw a box around each of the one or more spikelets in an image). The number of identified spikelets identified can be used in determining the heading start date. For example, the system can identify the first image, in a sequence of images captured during a crop growing season, where spikelets are detected. The system can determine the heading start date based on the date the first image containing spikelet(s) was captured. Additionally or alternatively, the number of spikelets identified can be used in determining the full heading date. For example, the system can track the number of spikelets in images taken of the same plants over multiple days, and identify the image where new spikelets stop developing (e.g., the number of spikelets in consecutive images remains stable). The system can determine the full heading date as the date corresponding to the image where new spikelets stop developing.

In some implementations, the system can generate daily heading values by normalizing the number of spikelets captured in an image. For instance, the number of spikelets can be normalized based on the number of spikelets on the heading start date and the number of spikelets on the full heading date. In some implementations, a growth curve can be generated based on daily heading values. In some implementations, the system can use one or more growth charts of daily heading values generated for one or more previous growing seasons to generate a daily heading value when, for example, the full season of growing data is not available. For instance, the system can determine the slope of the growth curve up until the current date. The daily heading value can be determined based on comparing the determined slope with the one or more growth charts for the one or more previous growing seasons.

Accordingly, various implementations set forth techniques for determining the number of spikelets in an image based on processing the image using a spikelet detection model, and determining a heading value for the image based on the number of identified spikelets. In contrast, conventional techniques require a human observer to visually inspect a cereal grain plot and make a determination of a heading value for the portion(s) of a cereal grain plot. When using conventional techniques, a first human observer may determine a different heading value than a second human observer when observing the same portion(s) of a plot of cereal grains. Techniques described herein can generate a more accurate and/or more consistent heading value compared to conventional techniques. More accurate crop yield predictions can be generated based on the more accurate heading value(s).

The above description is provided only as an overview of some implementations disclosed herein. These and other implementations of the technology are disclosed in additional detail below.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

DETAILED DESCRIPTION

Figure 1:
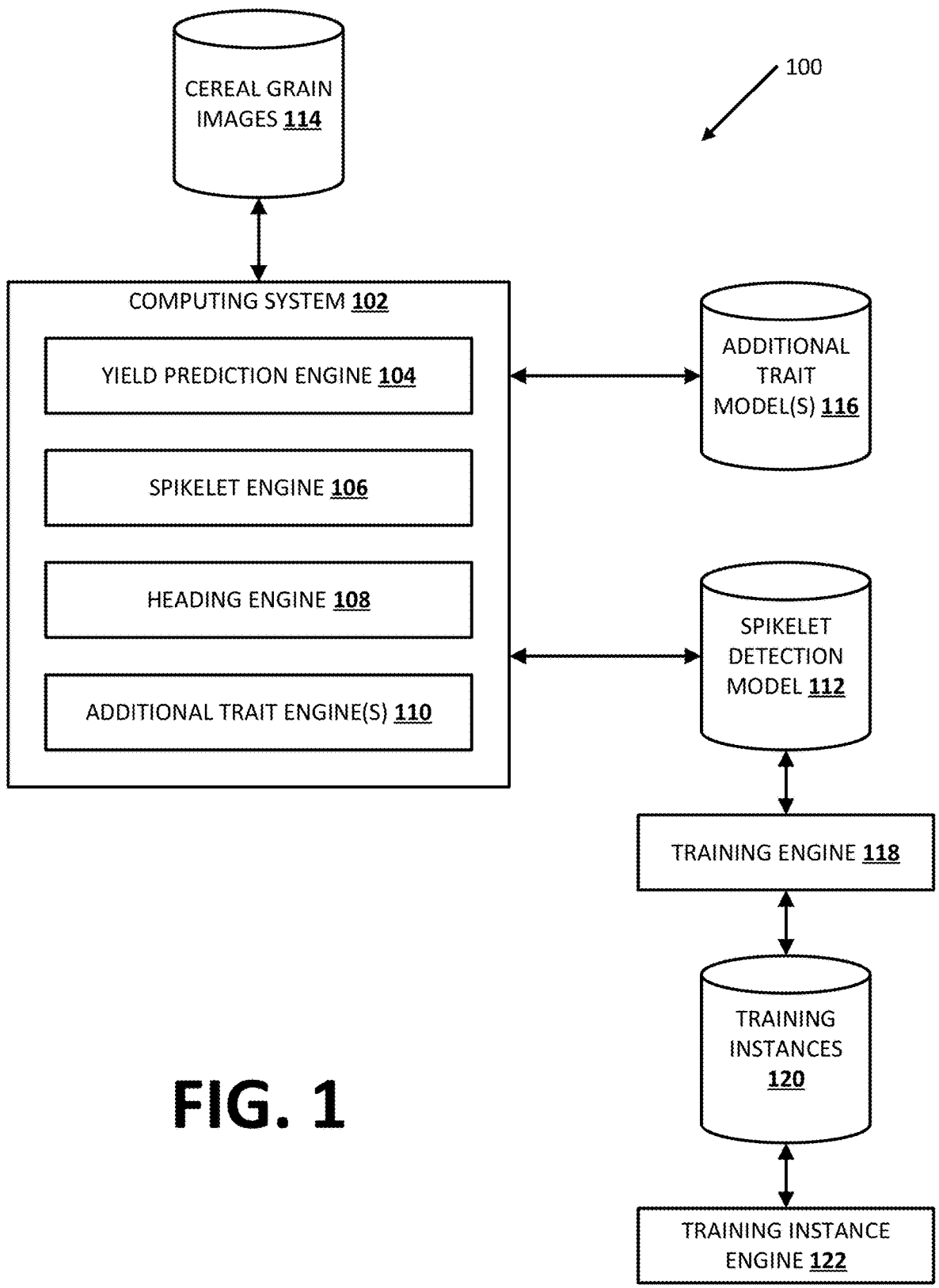
FIG. 1 illustrates an example environment in which various implementations disclosed herein may be implemented.

Turning now to the figures, FIG. 1 illustrates an example environment 100 in which implementations disclosed herein may be implemented. The example environment 100 includes a computing system 102 which can include a yield prediction engine 104, a spikelet engine 106, a heading engine 108, one or more additional trait engines 110, training engine 118, training instance engine 122, and/or one or more additional or alternative engines (not depicted). Additionally or alternatively, computing system 102 may be associated with cereal spikelet detection model 112, cereal grain images 114, one or more additional trait models 116, training instances 120, and/or one or more additional or alternative components (not depicted).

In some implementations, cereal grain images 114 can include images of one or more portions of a cereal grain plot. For example, the cereal grain plot can be captured in a single image and/or the cereal grain plot may be captured in multiple images (overlapping images and/or non-overlapping images). In some implementations, a sequence of images of the same portion(s) of the cereal grain plot can be captured during a growing season. For example, the sequence of images can include an image of the same portion of the cereal grain plot captured each day. The sequence of images can include images captured at additional and/or alternative frequencies, such as an image captured each minute, each hour, each day, twice a day, four times a day, every other day, every three days, every week, every month, at additional and/or alternative frequencies, and/or combinations thereof. In some implementations, the cereal grain images 114 can capture images of the same cereal grain plot across multiple growing seasons. For example, cereal grain images 114 can include one or more images of a plot captured during a first growing season and one or more images of the plot captured during a second growing season. Additionally or alternatively, cereal grain images 114 can include image(s) of multiple cereal grain plots. In some implementations, cereal grain images 114 can capture plots of multiple cereal grains. For example, cereal grain images 114 can include images of oats and images of corn.

Training instance engine 122 can be used to generate one or more training instances 120 for use in training spikelet detection model 112. In some implementations, a training instance 120 can include a cereal grain image portion and a ground truth portion, where the cereal grain image portion is an image capturing a cereal grain plant, and where the ground truth portion is an identification of the cereal grain plants in the cereal grain image portion. For example, the ground truth portion can include XY coordinates of one or more spikelets, one or more pixels associated with a spikelet, for example, by generating a box around pixel(s) associated with the spikelet, by changing the color of the pixel(s) associated with the spikelet (e.g., by changing the pixel(s) associated with a first spikelet to hot pink, changing the pixel(s) associated with a second spikelet to neon blue, changing the pixel(s) associated with a third spikelet to purple, etc.), by one or more additional or alternative identification method(s), and/or combinations thereof.

Spikelet detection model 112 can be a variety of neural network models including a feed forward neural network, a convolutional neural network, a recurrent neural network, a transformer network, one or more additional or alternative models, and/or combinations thereof. In some implementations, training engine 118 can be used to train spikelet detection model 112 based on one or more training instances 120. For example, training engine can process the cereal grain image portion of a training instance using spikelet detection model 112 to generate candidate output. Training engine 118 can determine a difference between the generated candidate output and the ground truth portion of the training instances. Additionally or alternatively, training engine 118 can update one or more portions of spikelet detection model 112 based on the determined difference.

Spikelet engine 106 can be used to process one or more of cereal grain images 114 to determine the number of spikelets in each image. In some implementations, spikelet engine 106 can process the image(s) using spikelet detection model 112 to identify one or more spikelets in the image(s). Additionally or alternatively, spikelet engine 106 can process the identified spikelets to determine the number of spikelets in each image.

In some implementations, heading engine 108 can be used to determine a heading value for one or more images. For example, a heading value can indicate the percentage of heading of the cereal grain plot captured in the image. In some implementations, heading engine 108 can determine a heading start date and/or a full heading date. In some of those implementations, the system can normalize the number of spikelets detected in an image based on the heading start date and/or full heading date, and can determine the heading value based on the normalized number of spikelets. Additionally or alternatively, the system can determine the heading value based on the number of spikelets identified in an image and a heading growth chart of the plot for one or more previous growing seasons. In some implementations, heading engine 108 can determine a heading value using process 300 of FIG. 3 and/or process 400 of FIG. 4.

In some implementations, one or more additional trait engines 110 can be used to determine one or more additional traits for one or more of the cereal grain images 114. For instance, the system can include a projected leaf area engine used to determine a projected leaf area value, a stand spacing engine used to determine a stand spacing value, a rust engine used to determine a wheat rust value, a maturity detection engine for determining a maturity detection value, an intercropping engine for determining an intercropping value, and/or additional or alternative engine(s) for determining additional trait value(s). In some implementations, one or more additional trait engines 110 can use one or more corresponding trait models (not depicted) for use in determining the corresponding trait value(s).

Yield prediction engine 104 can be used to determine a predicted cereal grain yield based on heading value(s) generated using heading engine 108. In some implementations, the predicted cereal grain yield can be generated based on heading value(s) and/or additional trait value(s) generated using one or more additional trait engines 110. For example, the system can determine the yield of the cereal grain plot based on one or more heading values, one or more projected leaf area values, one or more stand spacing values, one or more wheat rust values, one or more maturity detection values, one or more phenotyping value extracted from plots of cereal grains intercropped with other crops, one or more additional or alternative trait output values, and/or combinations thereof. In some implementations, trait output can be coupled with ground truth data (e.g., data collected from farmers) including the actual yield of a cereal grain plot. For example, the trait output and ground truth data can be used to train a regression model (not depicted) to generate the predicted yield output.

In some implementations, computing system 102 may include may include user interface input/output devices (not depicted), which may include, for example, a physical keyboard, a touch screen (e.g., implementing a virtual keyboard or other textual input mechanisms), a microphone, a camera, a display screen, and/or speaker(s). The user interface input/output devices may be incorporated with one or more computing system 102 of a user. For example, a mobile phone of the user may include the user interface input output devices; a standalone digital assistant hardware device may include the user interface input/output device; a first computing device may include the user interface input device(s) and a separate computing device may include the user interface output device(s); etc. In some implementations, all or aspects of computing system 102 may be implemented on a computing system that also contains the user interface input/output devices.

Some non-limiting examples of computing system 102 include one or more of: a desktop computing device, a laptop computing device, a standalone hardware device at least in part dedicated to an automated assistant, a tablet computing device, a mobile phone computing device, a computing device of a vehicle (e.g., an in-vehicle communications system, and in-vehicle entertainment system, an in-vehicle navigation system, an in-vehicle navigation system), or a wearable apparatus of the user that includes a computing device (e.g., a watch of the user having a computing device, glasses of the user having a computing device, a virtual or augmented reality computing device). Additional and/or alternative computing systems may be provided, such as one or more server computing systems that collectively form what is often referred to as a "cloud infrastructure" or simply "the cloud." Computing system 102 may include one or more memories for storage of data and software applications, one or more processors for accessing data and executing applications, and other components that facilitate communication over a network. The operations performed by computing system 102 may be distributed across multiple computing devices. For example, computing programs running on one or more computers in one or more locations can be coupled to each other through a network.

Figure 2:
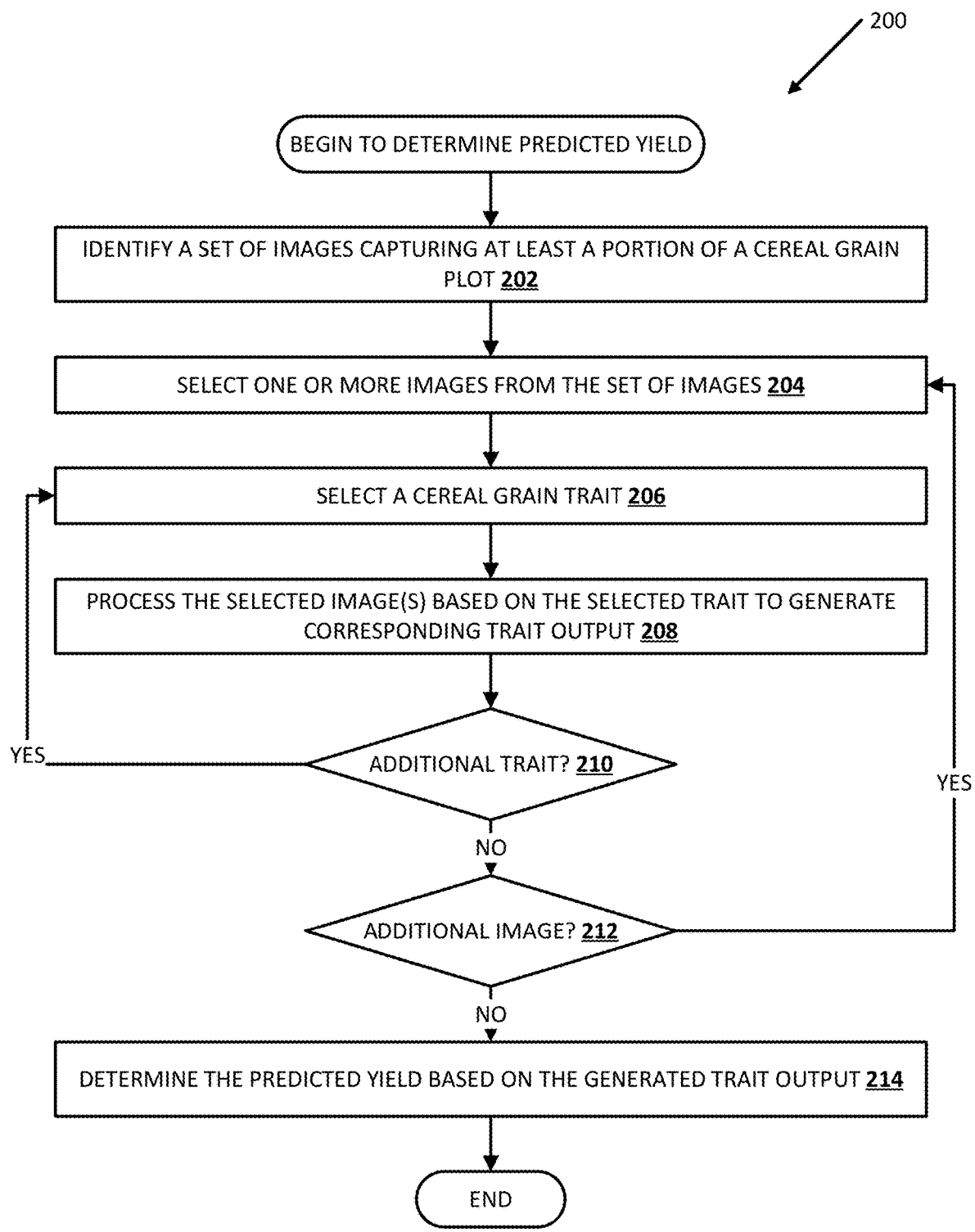
FIG. 2 illustrates an example process of determining a predicted yield for cereal grain in accordance with various implementations disclosed herein.

FIG. 2 is a flowchart illustrating an example process 200 of generating a predicted yield of a cereal grain plot in accordance with implementations disclosed herein. For convenience, the operations of the flowchart are described with reference to a system that performs the operations. This system may include various components of various computer systems, such as one or more components of computing system 150, and/or computing system 810. Moreover, while operations of process 200 are shown in a particular order, this is not meant to be limiting. One or more operations may be reordered, omitted, and/or added.

At block 202, the system identifies a set of images capturing at least a portion of a cereal grain plot. In some implementations, the set of images can capture the portion of the cereal grain plot over the entire growing season. As an example, the set of images can include an image of oats captured daily during the growing season. In some implementations, the set of images can capture the time from before the cereal grain crop is planted until after the cereal grain is harvested. However, this is merely illustrative and the set of images can capture a variety of dates including before the cereal grain is planted, the day the cereal grain is planted, the day after the cereal grain is planted, the day before the cereal grain begins growing, the day the cereal grain begins growing, the day before the cereal grain is ready for harvesting, the day the cereal grain is harvested, the day after the cereal grain is harvested, etc. In some implementations, the set of images can capture multiple portions of the same cereal grain plot. Additionally or alternatively, the set of images can capture multiple cereal grain plots.

At block 204, the system selects one or more images from the set of images. At block 206, the system selects a cereal grain trait. In some implementations, cereal grain traits can include heading, projected leaf area, stand spacing, wheat rust, maturity detection, phenotyping cereal grains intercropped with other crops, one or more additional or alternative traits, and/or combinations thereof.

At block 208, the system processes the selected image(s) based on the selected trait to generate corresponding trait output. For instance, the corresponding trait output for heading can be a heading value, for projected leaf area can be a projected leaf area value, for stand spacing can be a stand spacing value, for wheat rust can be a wheat rust value, for maturing detection can be a maturity detection value, for phenotyping cereal grains intercropped with other crops can be a phenotyping value extracted from cereal grains intercropped with other crops, etc. In some implementations, the system can process the image(s) to determine heading value(s). For example, the system can process image(s) to generate heading value(s) in accordance with process 300 of FIG. 3 and/or process 400 of FIG. 4.

The project leaf area trait can refer to the amount of visible leafy area relative to ground cover. In some implementations, it can be assumed that a plant's canopy completely occludes the ground by the end of the season, where the projected leaf area grows from a value of 0 at the beginning of the season to a value of 1 at season's end. The resulting curve may be valuable information for breeders, because it can be used as an approximation for the rate of growth of the plants. A slower growth curve may correlate with higher yields, as the plant can spend more time gathering nutrients before it shifts its focus to expending energy on growing seeds. In some implementations, a projected leaf area value can be determined by counting the number of green pixels in an image. For example, the system can process an image using color thresholding and/or additional or alternative image processing techniques to generate a bitmap dividing the image into green and non-green regions. In some implementations, the system should be robust to day-to-day variations in lighting, so using a color space such as a red, green, blue colorspace (RGB colorspace) may not be appropriate. In some of those implementations, the system can use a LAB encoding, as it separates lighting into a separate 'L' channel, allowing for a range of what is considered a green leaf pixels in the 'A' and 'B' channels.

In some implementations, the image may be preprocessed, for example using Gaussian blurring, image filtering, image padding, image transformation(s), additional and/or alternative preprocessing technique(s), and/or combinations thereof. Additionally or alternatively, the system may post-process the bitmap with morphology, image filtering, image padding, image transformation(s), one or more additional post-processing techniques, and/or combinations thereof. In some implementations, preprocessing and/or post-processing may be used to remove noise and/or smooth the resulting image. In some implementations, the system can determine the projected leaf area value by counting the number of green pixels in an image and calculating the average percentage of green in images in a plot. Furthermore, the system can generate a projected leaf area value for each plot. In some implementations, the system can generate a time series graph of change of projected leaf area value over time (i.e., a change as the leafy area in the plot grows).

The stand spacing trait can refer to the density of cereal grain plants (e.g., oat plants) that germinate early in the season. Since planting can be mechanized and consistent, variations in rates of germination between varieties may be indicative of a plant's ability to thrive in different soil conditions and/or share resources with other individuals. This trait may be represented as a count of plants per area in a plot, such as the number of plants per meter squared, the number of plants per foot squared, etc. In some implementations, the system can process image(s) using a plant detection model which may be used to identify individual plants at emergence.

In some implementations, the emergence stage can be chosen because at this point, any plants that have germinated are now visible, but they have not begun to crowd each other, so they are still distinguishable. In some implementations, the system can determine the number of instances of cereal grain plants in an image by processing the image using the plant detection model. Additionally or alternatively, the system can determine a density value by dividing the number of plants in the image by the actual area of the image. Furthermore, the system can determine the average stand spacing value for a plot based on determined density value(s). In some implementations, the system can generate a density heatmap within a plot.

Wheat rust is a disease to which many grains are susceptible. A plant afflicted by wheat rust may have a brownish/reddish discoloration. Breeders may want to select for varieties of plants that are wheat rust-resistant, as it is generally a sign of an unhealthy plant and can lead to lower yield. In some implementations, each plot can be assigned a rust score, such as a value from 0 to 1 indicating the degree of rust in a plot. In some implementations, the system can process the image using a wheat rust image classifier which has been to categorize one or more patches of the image as containing "no rust", "some rust", or "rust". The system can process image(s) in a plot by breaking the image(s) into patches and classifying each of the patches using the wheat rust image classifier. In some implementations, the system can determine a wheat rust score based on the classification of the patches. The final rust score may require the system to choose a date on which to run inference for the whole field and assign scores for each plot.

A cereal grain plant reaches maturity when it begins to brown and dry, which continues until harvest. In some implementations, the system can detect plant maturity and generate a plant maturity value by detecting brown pixels in an image in a manner similar to the detection of green pixels for projected leaf area. In some of those implementations, the system can utilize a minimum threshold of brown pixels that constitutes maturity.

Intercropping is the practice of planting two crops together in a plot. It can be a challenging problem space as the plants may be planted in high density, leading to noisy and crowded images, which can pose unique challenges to image-based machine learning tasks. In some implementations, one or more models can be used to extract visible traits from plots planted with a mixture of a cereal grain plant and peas (e.g., a mixture of oats and peas). In some implementations, the system can detect the same traits for the mixed cereal grain and pea plant plot such as stand spacing, heading, crown rust, and projected leaf area, in addition to new traits for peas, including flower count, flowering start data, flowering start date, number of pea pods.

In some implementations, the system may determine one or more traits using a semantic segmentation model, a deep learning methodology of training a model to classify each pixel in an image as belonging to a class. For example, the system can use a semantic segmentation model to classify pixels in an image as being "ground" or "leaf".

At block 210, the system determines whether to process the selected image(s) based on an additional cereal grain trait. In some implementations, the system can determine whether to process the selected image(s) based on additional cereal grain trait based on whether one or more conditions are satisfied, such as whether the system has generated trait output for a threshold number of traits, whether the system has generated output for each of the cereal grain traits, whether additional or alternative condition(s) are satisfied, and/or combinations thereof. If the system determines to process the selected image(s) based on an additional trait, the system proceeds back to block 206 to select an additional trait before proceeding to block 208 and generating additional corresponding trait output based on the selected additional trait. If not, the system proceeds to block 212.

At block 212, the system determines whether to process any additional images. In some implementations, the system can determine whether to process one or more additional images based on whether one or more conditions are satisfied, such as whether a threshold number of images have been processed, whether there are any remaining unprocessed images, whether one or more additional or alternative conditions have been satisfied, and/or a combination thereof. If the system determines to process one or more additional images, the system proceeds back to block 204 to select one or more additional images before proceeding back to blocks 206, 208, and 210 based on the one or more additional images. If not, the system proceeds to block 214.

At block 214, the system determines the predicted yield of the cereal grain plot based on the generated trait output. For example, the system can determine the yield of the cereal grain plot based on one or more heading values, one or more projected leaf area values, one or more stand spacing values, one or more wheat rust values, one or more maturity detection values, one or more phenotyping values extracted cereal grains intercropped with other crops, one or more additional or alternative trait output values, and/or combinations thereof. In some implementations, trait output can be coupled with ground truth data (e.g., data collected from farmers) including the actual yield of a cereal grain plot. For example, the trait output and ground truth data can be used to rain a regression model to generate the predicted yield output.

Figure 3:
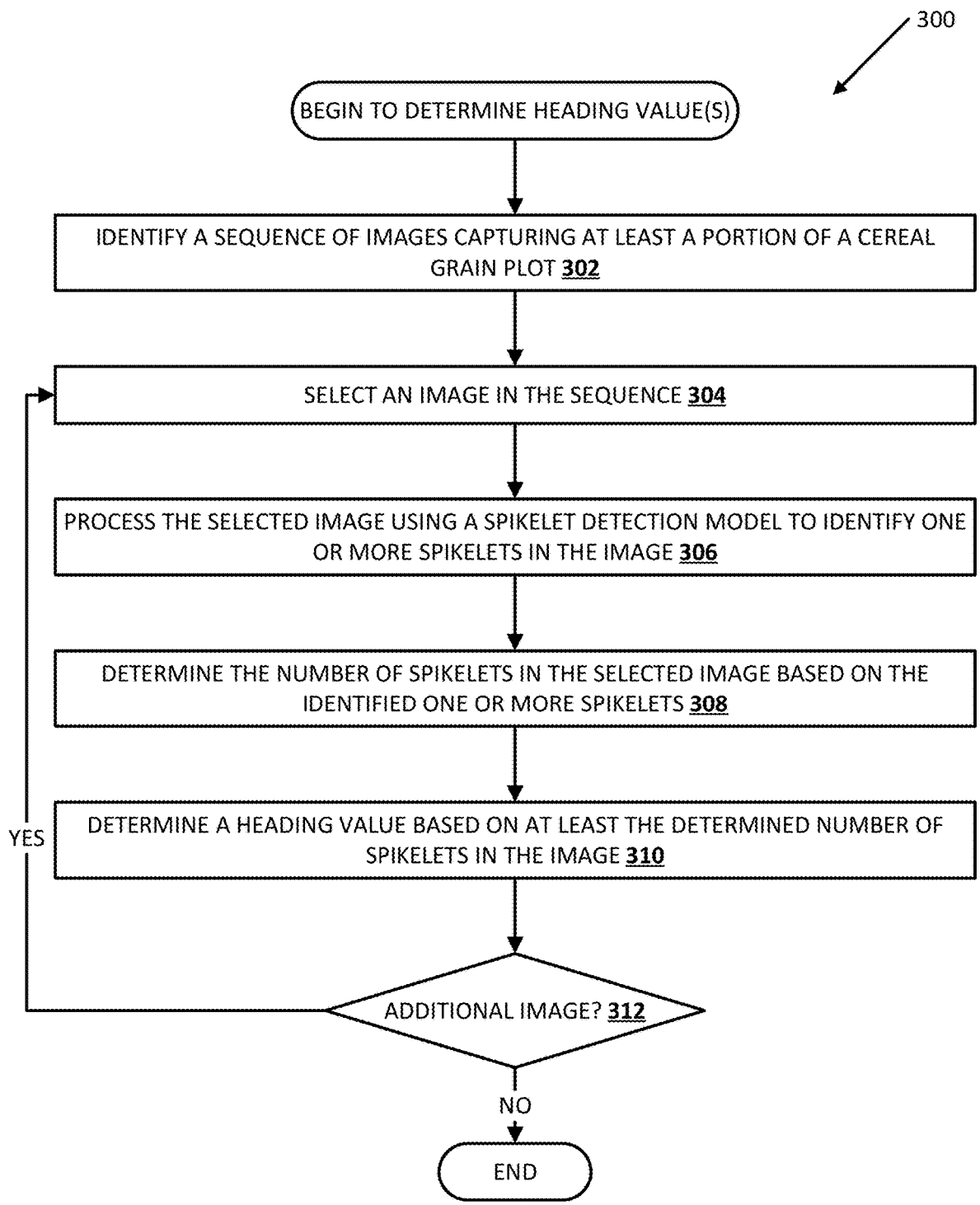
FIG. 3 illustrates an example process of determining one or more heading values in accordance with various implementations disclosed herein.

FIG. 3 is a flowchart illustrating an example process 300 of determining one or more heading values in accordance with implementations disclosed herein. For convenience, the operations of the flowchart are described with reference to a system that performs the operations. This system may include various components of various computer systems, such as one or more components of computing system 150, and/or computing system 810. Moreover, while operations of process 300 are shown in a particular order, this is not meant to be limiting. One or more operations may be reordered, omitted, and/or added.

At block 302, the system identifies a sequence of images capturing at least a portion of a cereal grain plot. In some implementations, the sequence of images can capture the portion of the cereal grain plot over the entire growing season. As an example, the sequence of images can include an image of oats captured daily during the growing season. In some implementations, the sequence of images can capture the time from before the cereal grain crop is planted until after the cereal grain is harvested. However, this is merely illustrative and the sequence of images can capture a variety of dates including before the cereal grain is planted, the day the cereal grain is planted, the day after the cereal grain is planted, the day before the cereal grain begins growing, the day the cereal grain begins growing, the day before the cereal grain is ready for harvesting, the day the cereal grain is harvested, the day after the cereal grain is harvested, etc.

At block 304, the system selects an image in the sequence. In some implementations, the system can select the next unprocessed image in the sequence. For example, in an initial iteration, the system can select the initial image in the sequence, in the second iteration, the system can select the second image in the sequence, in the third iteration, the system can select the third image in the sequence, etc. In some other implementations, the system can select an additional and/or alternative image.

At block 306, the system processes the selected image using a spikelet detection model to identify one or more spikelets in the image. In some implementations, the system can process the selected image using the spikelet detection model to generate the location of one or more spikelets in the image, for example, by generating XY coordinates for one or more spikelets. Additionally or alternatively, the system can identify one or more pixels associated with a spikelet, for example, by generating a box around pixel(s) associated with the spikelet, by changing the color of the pixel(s) associated with the spikelet (e.g., by changing the pixel(s) associated with a first spikelet to hot pink, changing the pixel(s) associated with a second spikelet to neon blue, changing the pixel(s) associated with a third spikelet to purple, etc.), by one or more additional or alternative identification method(s), and/or combinations thereof.

At block 308, the system determines the number of spikelets in the selected image based on the identified one or more spikelets. For example, when the system changes the color of groups of pixels associated with different spikelets at block 306, the system can identify the groups of colored pixels and determine the number of spikelets by counting the groups.

At block 310, the system determines a heading value based on at least the determined number of spikelets in the image. In some implementations, the system can determine the heading value based on the number of spikelets determined in block 308. Additionally or alternatively, in some implementations, the system can determine the image corresponding to the heading start date. For example, the system can determine the first image in the sequence with one or more spikelets. In other words, the heading start date can be the date where the system can first detect spikelet(s) in an image in the sequence. Additionally or alternatively, the system can determine the image in the sequence corresponding to the full heading date. In some implementations, the system can determine the change in the number of spikelets between an image and a previous image in the sequence (e.g., the change in the number of spikelets between the fourth image and the third image in the sequence). In some of those implementations, the system can determine the image where new spikelets stop developing based on when the number of spikelets in the image and the previous image stops changing.

Figure 7:
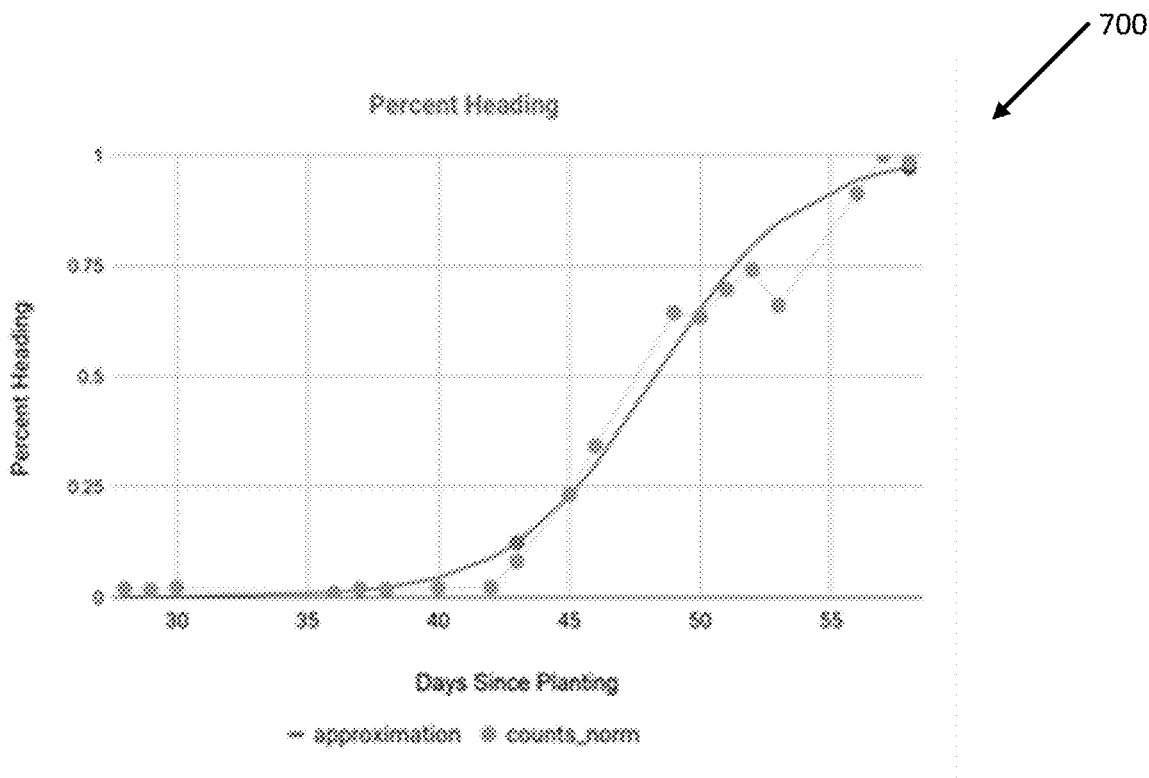
FIG. 7 illustrates an example heading growth chart in accordance with various implementations disclosed herein.

In some implementations, the system can normalize the number of spikelets in the image determined at block 308 based on the heading start image and/or the full heading image. For example, the number of spikelets can be normalized based on the number of spikelets in the heading start image and/or the number of spikelets in the full heading image. In some implementations, the system can determine the heading value based on the normalized number of spikelets. Additionally or alternatively, the system can generate a heading growth chart based on the normalized number of spikelets. An example heading growth chart in accordance with some implementations is illustrated in FIG. 7 herein. In some implementations, the system can determine the heading value based on the heading growth chart. In some implementations, the growth curve of the heading growth chart can be (approximately) sigmoid in nature.

At block 312, the system determines whether to process any additional images. In some implementations, the system can determine whether to process any additional images based on whether one or more conditions are satisfied such as whether there are any unprocessed images in the sequence of images, whether a threshold number of images have been processed, whether the system has identified the full heading date, whether one or more additional or alternative conditions have been satisfied, and/or combinations thereof. If the system determines to process an additional image, the system proceeds back to block 304 to select an additional image in the sequence before proceeding to blocks 306, 308, and 310 based on the additional image. In some implementations, the system can select the next image in the sequence of images as the additional image at block 304. If not, the process ends.

Figure 4:
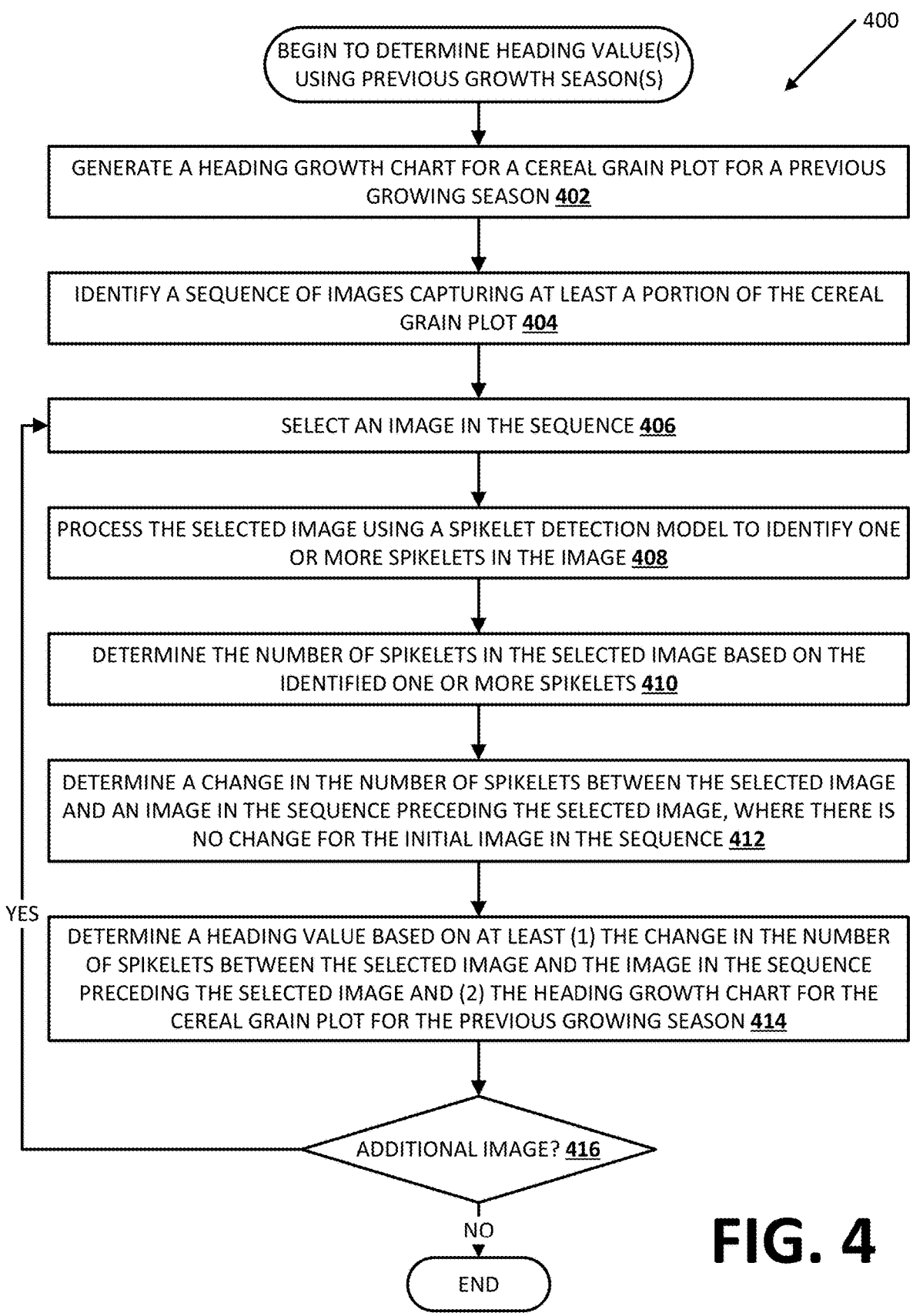
FIG. 4 illustrates another example process of determining one or more heading values in accordance with various implementations disclosed herein.

FIG. 4 is a flowchart illustrating an example process 400 of determining one or more heading values using one or more previous growth seasons in accordance with implementations disclosed herein. For convenience, the operations of the flowchart are described with reference to a system that performs the operations. This system may include various components of various computer systems, such as one or more components of computing system 150, and/or computing system 810. Moreover, while operations of process 400 are shown in a particular order, this is not meant to be limiting. One or more operations may be reordered, omitted, and/or added.

At block 402, the system generates a heading growth chart for a cereal grain plot for a previous growing season. In some implementations, the system can generate a heading growth chart based on processing a sequence of images capturing a previous growing season for the plot. In some of those implementations, the system can generate a heading growth chart for the previous season as described herein with respect to process 300 of FIG. 3. In some implementations, the system can access a previously generated heading growth chart for the previous growing season(s) stored locally at the system and/or stored remotely from the system.

At block 404, the system identifies a sequence of images capturing at least a portion of the cereal grain plot. In some implementations, the sequence of images captures the same portion(s) of the cereal grain plot used to generate the heading growth chart for the previous season(s) at block 402. In some implementations, the sequence of images does not capture an entire growing season. For example, the sequence of images can capture the first half of the growing season. In some implementations, the sequence of images can capture additional and/or alternative portion(s) of the growing season.

At block 406, the system selects an image in the sequence. In some implementations, the system can select the images in the order of the sequence. For example, the initial image selected at an initial iteration is the first image in the sequence, the second image selected at a second iteration is the second image in the sequence, the third image selected at a third iteration is the third image in the sequence, etc.

At block 408, the system processes the selected image using a spikelet detection model to identify one or more spikelets in the image. In some implementations, the system can process the selected image using the spikelet detection model to identify the one or more spikelets in the image in accordance with block 306 of FIG. 3.

At block 410, the system determines the number of spikelets in the selected image based on the identified one or more spikelets. In some implementations, the system can determine the number of spikelets in the selected image based on the identified one or more spikelets in accordance with block 308 of FIG. 3.

At block 412, the system determines a change in the number of spikelets between the selected image and an image in the sequence preceding the selected image, where there is no change for the initial image in the sequence. For example, the system can determine there are 10 spikelets in the third image in the sequence and there are 8 spikelets in the second image in the sequence. In the illustrated example, the system can determine a change of two spikelets between the second and third images in the sequence.

At block 414, the system determines a heading value for the selected image based on at least (1) the change in the number of spikelets between the selected image and the image in the sequence preceding the selected image and (2) the heading growth chart for the cereal grain plot for the previous growing season. For example, in some implementations, the system can determine the slope of the heading growth chart for the portion of the current growing season captured in the sequence of images based on the change in spikelets between images in the sequence. In some of those implementations, the heading growth chart curve can be (approximately) sigmoid in nature. The system can determine the heading value based on comparing the heading growth chart for the current season with the heading growth chart for the previous season(s). For example, by determining whether the cereal grain plants are growing rapidly (e.g., a large increase in the number of spikelets between images in the sequence) or are growing slowly (e.g., a small increase in the number of spikelets between images in the sequence), the system can determine the stage of heading of the image.

At block 416, the system determines whether to process any additional images. In some implementations, the system can determine whether to process any additional images based on whether one or more conditions are satisfied such as whether there are any unprocessed images in the sequence of images, whether a threshold number of images have been processed, whether the system has identified the full heading date, whether one or more additional or alternative conditions have been satisfied, and/or combinations thereof. If the system determines to process an additional image, the system proceeds back to block 406 to select an additional image in the sequence before proceeding to blocks 408, 410, 412, and 414 based on the additional image. In some implementations, the system can select the next image in the sequence as the additional image in block 406. If not, the process ends.

Figure 5:
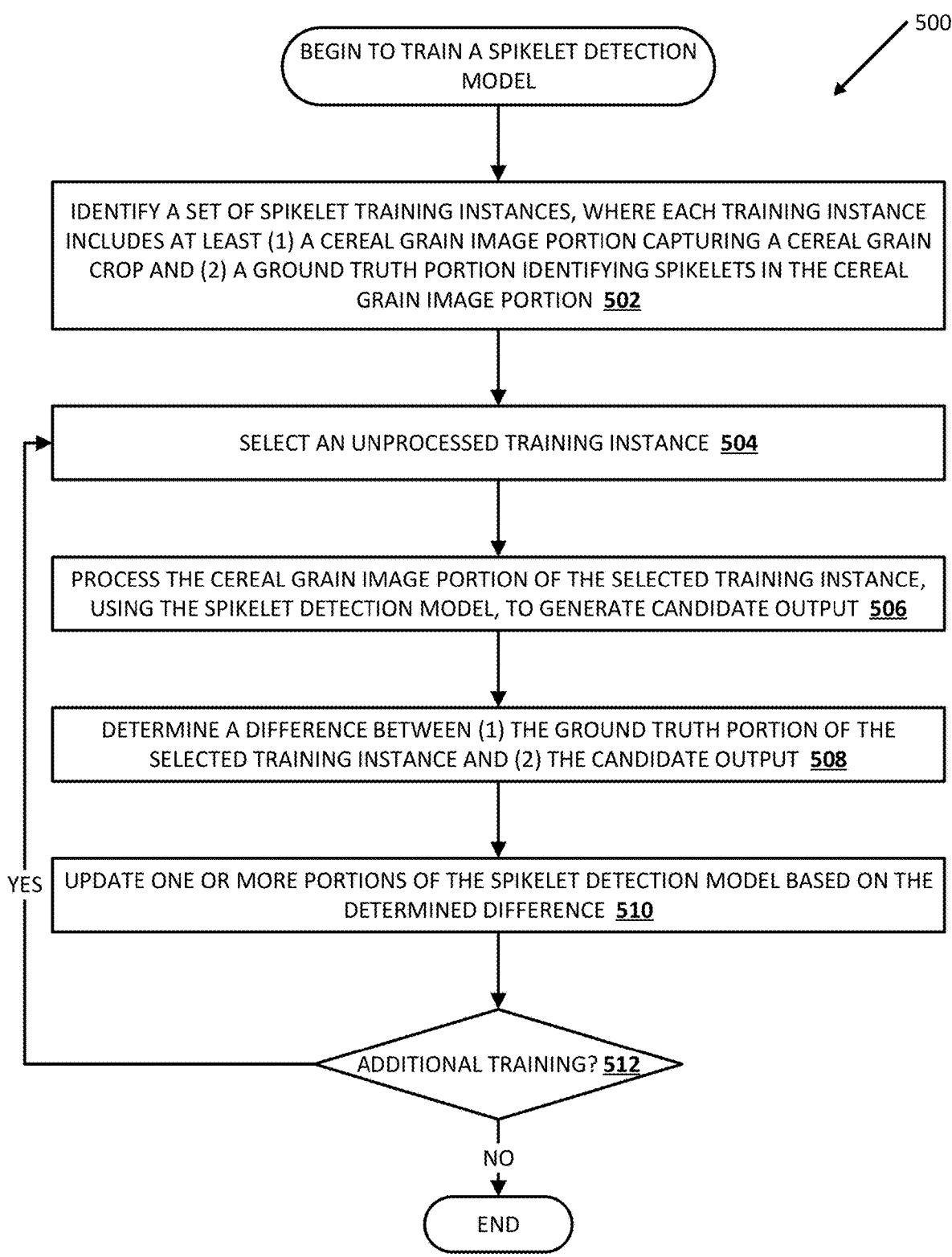
FIG. 5 illustrates an example process of training a spikelet detection model in accordance with various implementations disclosed herein.

FIG. 5 is a flowchart illustrating an example process 500 of training a spikelet detection model in accordance with implementations disclosed herein. For convenience, the operations of the flowchart are described with reference to a system that performs the operations. This system may include various components of various computer systems, such as one or more components of computing system 150, and/or computing system 810. Moreover, while operations of process 500 are shown in a particular order, this is not meant to be limiting. One or more operations may be reordered, omitted, and/or added.

At block 502, the system identifies a set of spikelet training instances, where each training instance includes at least (1) a cereal grain image portion capturing a cereal grain crop and (2) a ground truth portion identifying spikelets in the cereal grain image portion. In some implementations, the system ground truth portion can include XY coordinates for one or more spikelets, one or more pixels associated with a spikelet, for example, by generating a box around pixel(s) associated with the spikelet, by changing the color of the pixel(s) associated with the spikelet (e.g., by changing the pixel(s) associated with a first spikelet to hot pink, changing the pixel(s) associated with a second spikelet to neon blue, changing the pixel(s) associated with a third spikelet to purple, etc.), by one or more additional or alternative identification method(s), and/or combinations thereof.

At block 504, the system selects an unprocessed training instance.

At block 506, the system processes the cereal grain image portion of the selected training instance, using the spikelet detection model, to generate candidate output. In some implementations, the candidate output can identify one or more candidate spikelets in the cereal grain image portion of the selected training instance.

At block 508, the system determines a difference between (1) the ground truth portion of the selected training instance and (2) the candidate output.

At block 510 the system updates one or more portions of the spikelet detection model based on the determined difference. For example, in some implementations, the system can update the weight(s) of one or more portions of the spikelet detection model using backpropagation.

At block 512, the system determines whether to perform any additional training. If so, the system proceeds back to block 504 to select an additional unprocessed training instance before proceeding to blocks 506, 508, and 510 based on the additional training instance. In some implementations, the system can determine to perform more training if there are one or more additional unprocessed training instances and/or if other criterion/criteria are not yet satisfied. The other criterion/criteria can include, for example, whether a threshold number of epochs have occurred and/or a threshold duration of training has occurred. Although process 500 is described with respect to a non-batch learning technique, batch learning may additionally and/or alternatively be utilized. If, at block 512 the system determines not to perform more training, the process can end.

Figure 6:
FIG. 6 illustrates example output generated by processing an image using a spikelet detection model in accordance with various implementations disclosed herein.

FIG. 6 illustrates an example image of a portion of a cereal grain plot. Image 600 captures oat plants. In the illustrated example, the spikelets of the oat plants are identified by rectangular bounding boxes drawn around the spikelets. In some implementations, image 600 can be output generated by a spikelet detection model based on processing a corresponding image using the spikelet detection model. In some other implementations, image 600 can be a ground truth representation portion of a training instance, where the ground truth representation portion identifies the location of spikelets (e.g., using bounding shapes) in a cereal grain image portion of the training instance. In some such implementations, the ground truth portion of the training instance can be generated by one or more human reviewers drawing the bounding boxes around the spikelets in the cereal grain image.

FIG. 7 illustrates an example heading growth chart 700 in accordance with implementations disclosed herein. In the illustrated example, heading growth chart 700 includes a plot of heading values over time, represented as a percent heading over days since planting. In some implementations, the heading value can be normalized, for example by the heading start date and/or the full heading date. A growth curve can be generated based on the heading values over time. Heading growth chart 700 includes an approximate growth curve. In the illustrated example, the approximate growth curve is sigmoid in nature.

Figure 8:
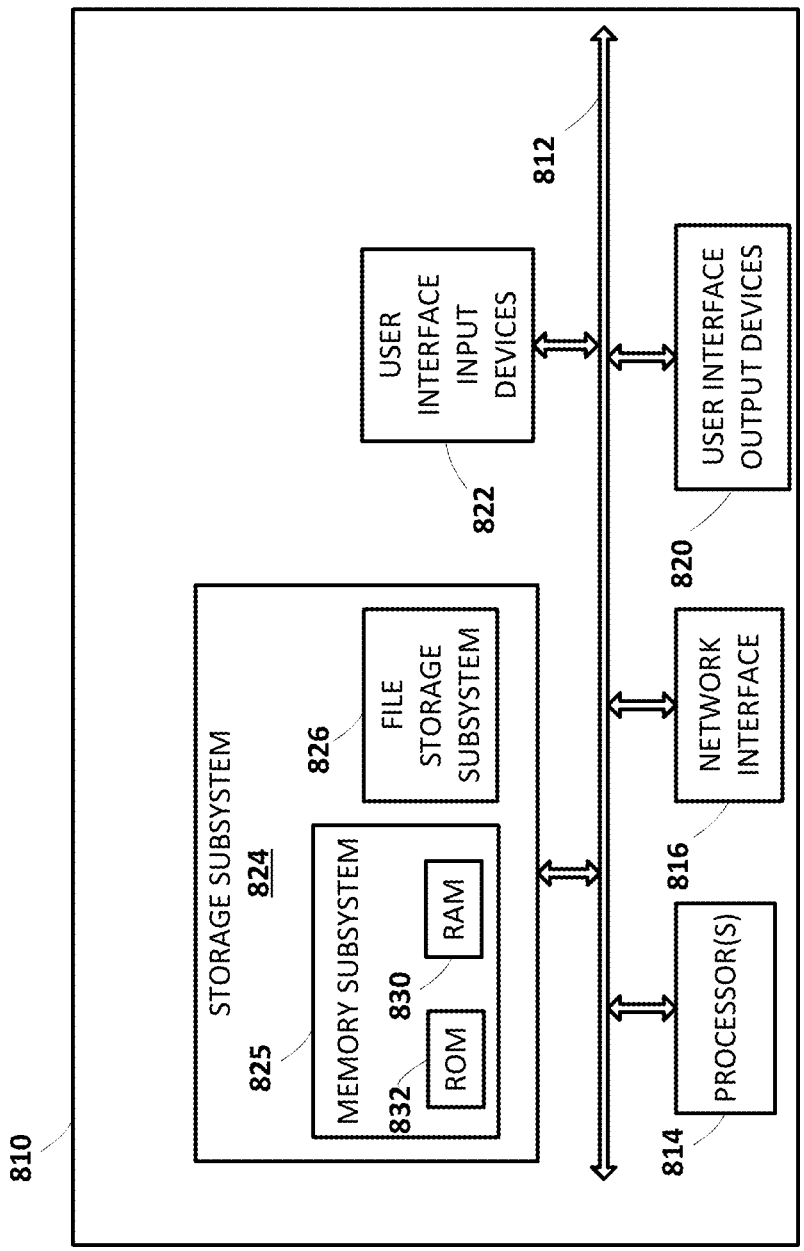
FIG. 8 illustrates an example architecture of a computing device.

FIG. 8 is a block diagram of an example computing device 810 that may optionally be utilized to perform one or more aspects of techniques described herein. In some implementations, one or more of a client computing device, and/or other component(s) may comprise one or more components of the example computing device 810.

Computing device 810 typically includes at least one processor 814 which communicates with a number of peripheral devices via bus subsystem 812. These peripheral devices may include a storage subsystem 824, including, for example, a memory subsystem 825 and a file storage subsystem 826, user interface output devices 820, user interface input devices 822, and a network interface subsystem 816. The input and output devices allow user interaction with computing device 810. Network interface subsystem 816 provides an interface to outside networks and is coupled to corresponding interface devices in other computing devices.

User interface input devices 822 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computing device 810 or onto a communication network.

User interface output devices 820 may include a display subsystem, a printer, a fax machine, or non-visual displays such as audio output devices. The display subsystem may include a cathode ray tube ("CRT"), a flat-panel device such as a liquid crystal display ("LCD"), a projection device, or some other mechanism for creating a visible image. The display subsystem may also provide non-visual display such as via audio output devices. In general, use of the term "output device" is intended to include all possible types of devices and ways to output information from computing device 810 to the user or to another machine or computing device.

Storage subsystem 824 stores programming and data constructs that provide the functionality of some or all of the modules described herein. For example, the storage subsystem 824 may include the logic to perform selected aspects of one or more of the processes of FIG. 2, FIG. 3, FIG. 4 and/or FIG. 5, as well as to implement various components depicted in FIG. 113.

These software modules are generally executed by processor 814 alone or in combination with other processors. Memory 825 used in the storage subsystem 824 can include a number of memories including a main random access memory ("RAM") 830 for storage of instructions and data during program execution and a read only memory ("ROM") 832 in which fixed instructions are stored. A file storage subsystem 826 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 826 in the storage subsystem 824, or in other machines accessible by the processor(s) 814.

Bus subsystem 812 provides a mechanism for letting the various components and subsystems of computing device 810 communicate with each other as intended. Although bus subsystem 812 is shown schematically as a single bus, alternative implementations of the bus subsystem may use multiple busses.

Computing device 810 can be of varying types including a workstation, server, computing cluster, blade server, server farm, or any other data processing system or computing device. Due to the ever-changing nature of computers and networks, the description of computing device 810 depicted in FIG. 8 is intended only as a specific example for purposes of illustrating some implementations. Many other configurations of computing device 810 are possible having more or fewer components than the computing device depicted in FIG. 8.

In situations in which the systems described herein collect personal information about users (or as often referred to herein, "participants"), or may make use of personal information, the users may be provided with an opportunity to control whether programs or features collect user information (e.g., information about a user's social network, social actions or activities, profession, a user's preferences, or a user's current geographic location), or to control whether and/or how to receive content from the content server that may be more relevant to the user. Also, certain data may be treated in one or more ways before it is stored or used, so that personal identifiable information is removed. For example, a user's identity may be treated so that no personal identifiable information can be determined for the user, or a user's geographic location may be generalized where geographic location information is obtained (such as to a city, ZIP code, or state level), so that a particular geographic location of a user cannot be determined. Thus, the user may have control over how information is collected about the user and/or used.

In some implementations, a method implemented by one or more processors is provided, the method including for each image in a sequence of images, capturing at least a portion of a cereal grain plot during a growing season, determining the number of cereal grain spikelets in the image, wherein determining the number of cereal grain spikelets in the image includes processing the image using a spikelet detection model to identify one or more cereal grain spikelets in the image. The method further includes determining a number of spikelets in the image based on the identified one or more cereal grain spikelets. The method further includes determining a heading value for the image based on at least the number of spikelets in the image. The method further includes determining a predicted yield for the cereal grain plot based on at least one or more of the determined heading values.

These and other implementations of the technology disclosed herein can include one or more of the following features.

In some implementations, the sequence of images capturing at least a portion of a cereal grain plot during a growing season captures the entire growing season. In some of those implementations, determining the heading value for the image based on at least the number of spikelets in the image includes determining a heading start image in the sequence of images, capturing the beginning of heading in the cereal grain plot. In some of those implementations, the method further includes determining a full heading image in the sequence of images, capturing full heading in the cereal grain plot. In some of those implementations, the method further includes determining the heading value for the image based on the number of spikelets in the heading start image and based on the number of spikelets in the full heading image.

In some implementations, the sequence of images capturing at least a portion of a cereal grain plot during a growing season captures a portion of the growing season less than the entire growing season. In some of those implementations, the determining the heading value for the image based on at least the number of spikelets in the image includes determining a change in the number of spikelets in the image and the number of spikelets in one or more previous images in the sequence. In some of those implementations, the method further includes comparing the change in the number of spikelets with a heading value growth chart for one or more previous growing seasons. In some of those implementations, the method further includes determining the heading value for the image based on the comparing.

In some implementations, the cereal grain plot includes wheat, maize, rice, barley, oats, rye, and/or sorghum.

In some implementations, prior to processing the image using the spikelet detection model, the method further includes training the spikelet detection model. In some of those implementations, training the spikelet detection model includes, for each of a plurality of training instances and until one or more conditions are satisfied, processing a training image portion of the training instance using the spikelet detection model to generate candidate output identifying one or more candidate spikelets in the training image. In some of those implementations, the method further includes determining a difference between the candidate output and a ground truth portion of the training instance, where the ground truth portion of the training instance identifies one or more spikelets in the training image. In some of those implementations, the method further includes updating one or more portions of the spikelet detection model based on the determined difference.

In some implementations, the method further includes processing at least one image of the sequence of images using a convolutional neural network to determine a measure of wheat rust prevalence in the image, wherein the predicted yield for the cereal grain plot is further based on the measure of wheat rust prevalence.

In some implementations, the method further includes processing at least one image of the sequence of images to determine a measure of stand spacing, wherein the predicted yield for the cereal grain plot is further based on the measure of stand spacing.

In addition, some implementations include one or more processors (e.g., central processing unit(s) (CPU(s)), graphics processing unit(s) (GPU(s)), and/or tensor processing unit(s) (TPU(s)) of one or more computing devices, where the one or more processors are operable to execute instructions stored in associated memory, and where the instructions are configured to cause performance of any of the methods described herein. Some implementations also include one or more transitory or non-transitory computer readable storage media storing computer instructions executable by one or more processors to perform any of the methods described herein.

What is claimed is:

1. A method implemented by one or more processors, the method comprising: for an image of at least a portion of a cereal grain plot in a sequence of images captured during a portion of a growing season less than an entire growing season, determining, by at least one processor circuit programmed by at least one instruction, a number of cereal grain spikelets in the image, wherein determining the number of cereal grain spikelets in the image includes: processing the image to determine a trait of a plant in the image of the cereal grain plot, wherein processing the image includes: using a spikelet detection model to identify one or more cereal grain spikelets in the image, the spikelet detection model to identify the one or more cereal grain spikelets in the image based on a training instance, the training instance to train the spikelet detection model using a training image portion and a ground truth image portion, the ground truth image portion to include an identification of a position of a cereal grain spikelet of a cereal grain plant shown in the training image portion; and generating a bitmap including a green region and a non-green region of the image, wherein the non-green region corresponds to a maturity of a plant of the cereal grain plot; and determining the number of cereal grain spikelets in the image based on the identified one or more cereal grain spikelets and the bitmap; determining a heading value for the image based on at least the number of cereal grain spikelets in the image, wherein determining the heading value for the image based on at least the number of cereal grain spikelets in the image includes: determining a change between the number of cereal grain spikelets in the image and the number of cereal grain spikelets in one or more previous images in the sequence; comparing the change in the number of cereal grain spikelets with a heading growth chart of the cereal grain plot for one or more previous growing seasons, where the heading growth chart is based on processing of a previous sequence of images capturing a previous growing season for the cereal grain plot; and determining the heading value for the image based on the comparison; and determining, by one or more of the at least one processor circuit, a predicted yield for the cereal grain plot based on at least one or more of the determined heading values.

2. The method of claim 1, wherein the cereal grain plot includes wheat, maize, rice, barley, oats, rye, and/or sorghum.

3. The method of claim 1, further including, prior to processing the image using the spikelet detection model, training the spikelet detection model, wherein training the spikelet detection model includes: processing the training image portion of the training instance using the spikelet detection model to generate a candidate output identifying one or more candidate cereal grain spikelets in a training image; determining a difference between the candidate output and the ground truth image portion of the training instance; and updating one or more portions of the spikelet detection model based on the determined difference.

4. The method of claim 1, further including processing at least one image of the sequence of images using a convolutional neural network to determine a measure of wheat rust prevalence in the image, wherein the predicted yield for the cereal grain plot is further based on the measure of wheat rust prevalence.

5. The method of claim 1, further including processing at least one image of the sequence of images to determine a measure of stand spacing, wherein the predicted yield for the cereal grain plot is further based on the measure of stand spacing.

6. A non-transitory computer readable storage medium configured to store instructions that, when executed by one or more processors, cause the one or more processors to: for an image of at least a portion of a cereal grain plot in a sequence of images captured during a portion of a growing season less than an entire growing season, determine a number of cereal grain spikelets in the image, wherein to determine the number of cereal grain spikelets in the image includes to: process the image to determine a trait of a plant in the image of the cereal grain plot, wherein to process the image includes to: use a spikelet detection model to identify one or more cereal grain spikelets in the image, the spikelet detection model to identify the one or more cereal grain spikelets in the image based on a training instance, the training instance to train the spikelet detection model using a training image portion and a ground truth image portion, the ground truth image portion to include an identification of a position of a cereal grain spikelet of a cereal grain plant shown in the training image portion; and generate a bitmap including a green region and a non-green region of the image, wherein the non-green region corresponds to a maturity of a plant of the cereal grain plot; and determine the number of cereal grain spikelets in the image based on the identified one or more cereal grain spikelets and the bitmap; determine a heading value for the image based on at least the number of cereal grain spikelets in the image, wherein to determine the heading value for the image based on at least the number of cereal grain spikelets in the image includes to: determine a change between the number of cereal grain spikelets in the image and the number of cereal grain spikelets in one or more previous images in the sequence; compare the change in the number of cereal grain spikelets with a heading growth chart of the cereal grain plot for one or more previous growing seasons, where the heading growth chart is based on processing of a previous sequence of images capturing a previous growing season for the cereal grain plot; and determine the heading value for the image based on the comparison; and determine a predicted yield for the cereal grain plot based on at least one or more of the determined heading values.

7. The non-transitory computer readable storage medium of claim 6, wherein the cereal grain plot includes wheat, maize, rice, barley, oats, rye, and/or sorghum.

8. The non-transitory computer readable storage medium of claim 6, wherein the instructions are to cause the one or more processors to prior to processing the image using the spikelet detection model, train the spikelet detection model, wherein to train the spikelet detection model the one or more processors are to: process the training image portion of the training instance using the spikelet detection model to generate a candidate output identifying one or more candidate cereal grain spikelets in a training image; determine a difference between the candidate output and the ground truth image portion of the training instance; and update one or more portions of the spikelet detection model based on the determined difference.

9. The non-transitory computer readable storage medium of claim 6, wherein the instructions are to cause the one or more processors to process at least one image of the sequence of images using a convolutional neural network to determine a measure of wheat rust prevalence in the image, wherein the predicted yield for the cereal grain plot is further based on the measure of wheat rust prevalence.

10. The non-transitory computer readable storage medium of claim 6, wherein the instructions are to cause the one or more processors to process at least one image of the sequence of images to determine a measure of stand spacing, wherein the predicted yield for the cereal grain plot is further based on the measure of stand spacing.

11. A computing device, comprising: one or more processors, and memory configured to store instructions that, when executed by the one or more processors, cause the one or more processors to: for an image of at least a portion of a cereal grain plot in a sequence of images captured during a portion of a growing season less than an entire growing season, determine a number of cereal grain spikelets in the image, wherein to determine the number of cereal grain spikelets in the image includes to: process the image to determine a trait of a plant in the image of the cereal grain plot, wherein to process the image includes to: use a spikelet detection model to identify one or more cereal grain spikelets in the image, the spikelet detection model to identify the one or more cereal grain spikelets in the image based on a training instance, the training instance to train the spikelet detection model using a training image portion and a ground truth image portion, the ground truth image portion to include an identification of a position of a cereal grain spikelet of a cereal grain plant shown in the training image portion; and generate a bitmap including a green region and a non-green region of the image, wherein the non-green region corresponds to a maturity of a plant of the cereal grain plot; and determine the number of spikelets in the image based on the identified one or more cereal grain spikelets and the bitmap; determine a heading value for the image based on at least the number of cereal grain spikelets in the image, wherein to determine the heading value for the image based on at least the number of cereal grain spikelets in the image includes to: determine a change between the number of cereal grain spikelets in the image and the number of cereal grain spikelets in one or more previous images in the sequence; compare the change in the number of cereal grain spikelets with a heading growth chart of the cereal grain plot for one or more previous growing seasons, where the heading growth chart is based on processing of a previous sequence of images capturing a previous growing season for the cereal grain plot; and determine the heading value for the image based on the comparison; and determine a predicted yield for the cereal grain plot based on at least one or more of the determined heading values.

12. The computing device of claim 11, wherein the cereal grain plot includes wheat, maize, rice, barley, oats, rye, and/or sorghum.

13. The computing device of claim 11, wherein the one or more processors is to, prior to processing the image using the spikelet detection model, train the spikelet detection model, wherein to train the spikelet detection model includes to: process the training image portion of the training instance using the spikelet detection model to generate a candidate output identifying one or more candidate cereal grain spikelets in a training image; determine a difference between the candidate output and the ground truth image portion of the training instance; and update one or more portions of the spikelet detection model based on the determined difference.

14. The computing device of claim 11, wherein the one or more processors is to process at least one image of the sequence of images using a convolutional neural network to determine a measure of wheat rust prevalence in the image, wherein the predicted yield for the cereal grain plot is further based on the measure of wheat rust prevalence.

* * * * *